United States Patent [19]

Burnham

[11] Patent Number: 5,335,410
[45] Date of Patent: Aug. 9, 1994

[54] METHOD OF MAKING ULTRA SMALL DIAMETER CATHETERS AND OF REINFORCED TUBULAR PRODUCT

[76] Inventor: Warren R. Burnham, 10036 Saratoga Rd., South Glen Falls, N.Y. 12803

[21] Appl. No.: 31,329

[22] Filed: Mar. 15, 1993

[51] Int. Cl.$^5$ .................. B23P 11/02; B32B 31/30; D01D 5/24
[52] U.S. Cl. ..................... 29/452; 29/33 D; 29/DIG. 24; 264/173; 264/174
[58] Field of Search .................. 29/33 D, 402.21, 405, 29/450, 451, 452, 460, 527.1, 777, DIG. 42, DIG. 47, 33 T, 240, 456, 526.3, DIG. 21, DIG. 24; 264/172, 173, 174, 103; 425/113, 114; 604/95, 96, 280, 281, 282

[56] References Cited

U.S. PATENT DOCUMENTS

| | | | |
|---|---|---|---|
| 2,989,778 | 6/1961 | Frenkel | 425/113 X |
| 3,249,666 | 5/1966 | French | 264/173 X |
| 3,419,010 | 12/1968 | Williamson | 604/281 |
| 3,428,046 | 2/1969 | Remer et al. | 604/96 X |
| 3,558,754 | 1/1971 | M. Martin | 264/173 X |
| 3,585,707 | 6/1971 | Stevens | 29/527.1 X |
| 3,618,613 | 11/1971 | Schulte | 604/282 |
| 3,783,454 | 1/1974 | Sausse et al. | 604/280 X |
| 3,961,873 | 6/1976 | Brown | 425/114 |
| 4,135,869 | 1/1979 | Loyer | 264/173 X |
| 4,219,522 | 8/1980 | Oyama | 29/460 X |
| 4,271,587 | 6/1981 | Shields | 29/777 X |
| 4,321,226 | 3/1982 | Markling | 264/163 X |
| 4,705,511 | 11/1987 | Kocak | 604/282 |
| 4,764,324 | 8/1988 | Burnham | 264/174 X |
| 4,832,681 | 5/1989 | Lenck | 604/282 X |
| 4,917,666 | 4/1990 | Solar et al. | 604/96 X |
| 4,927,413 | 5/1990 | Hess | 604/95 |
| 4,950,232 | 8/1990 | Ruzicka et al. | 604/282 X |
| 4,955,859 | 9/1990 | Zilber | 604/280 X |
| 4,955,862 | 9/1990 | Sepetka | 604/282 X |

FOREIGN PATENT DOCUMENTS

| | | |
|---|---|---|
| 899206 | 7/1984 | Belgium . |
| 102422 | 3/1984 | European Pat. Off. . |
| 2613782 | 10/1977 | Fed. Rep. of Germany . |
| 88908506 | 12/1983 | PCT Int'l Appl. . |
| 1349843 | 4/1974 | United Kingdom . |
| 1584616 | 2/1981 | United Kingdom . |

*Primary Examiner*—Peter Dungba Vo
*Attorney, Agent, or Firm*—Ronald P. Kananen

[57] ABSTRACT

An ultra small diameter reinforced catheter or tubular product is produced by winding reinforcing stands on the surface of a plastic tube and introducing the same into a heated die which compresses the strands against the tubing and at the same time heats and softens superficial portions of the tubing wall with simultaneously applying both conductive and radiant heat. This allows the strands to sink into the tubing wall. Following this, the compression and the conductive heating a removed while the tubing continues to be exposed to radiant heat from the die. During this last stage, the tension in the strands induces the strands to assume a predetermined position between the inner and outer surfaces of the tubing.

7 Claims, 3 Drawing Sheets

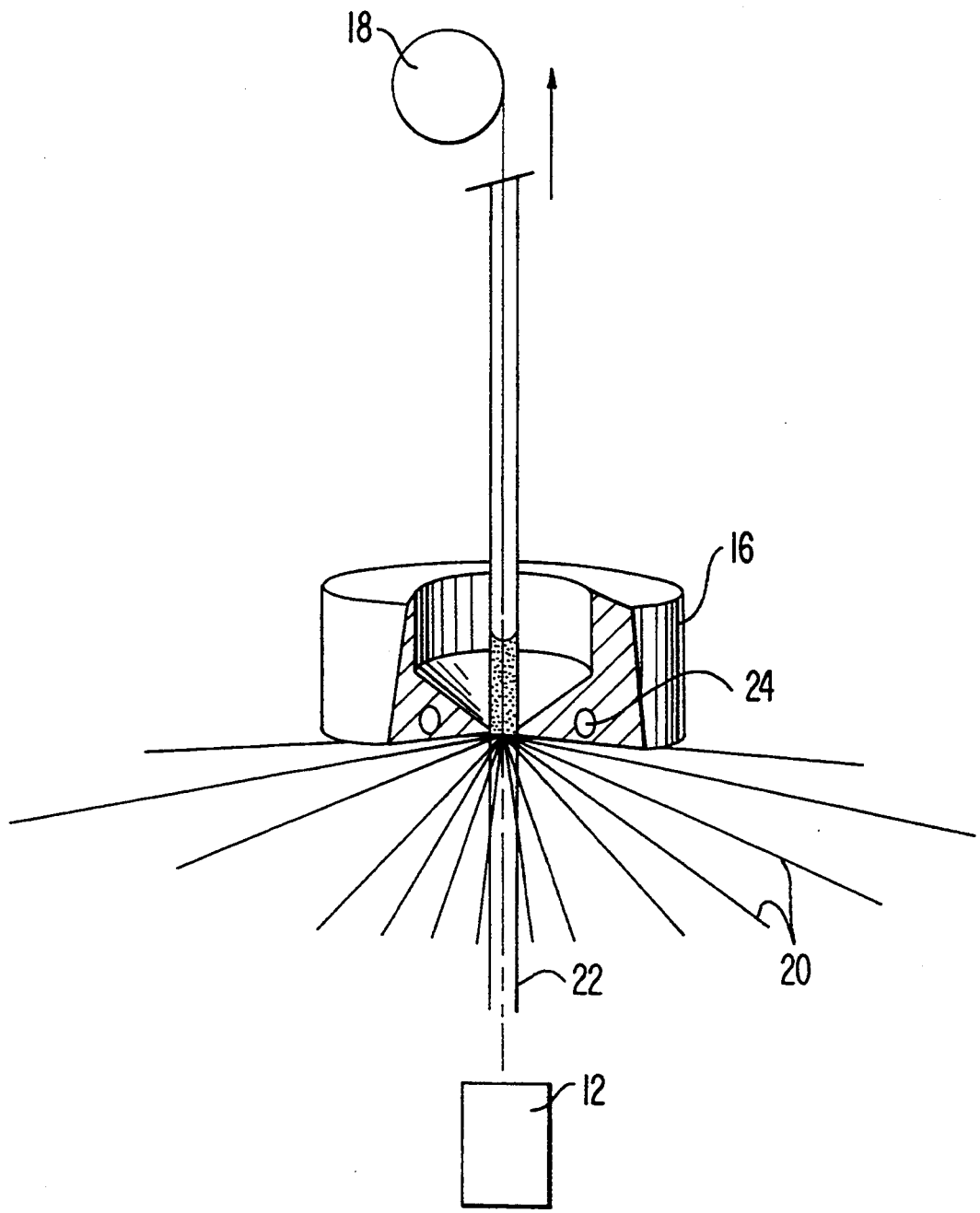

METHOD OF MAKING ULTRA SMALL DIAMETER CATHETERS AND OF REINFORCED TUBULAR PRODUCT

BACKGROUND OF THE INVENTION

1. Field of the Invention

The present invention relates generally to the formation of reinforced tubing and more specifically to small diameter reinforced pipe/tubing which can be used as a catheter and the like type of medical instrument.

2. Description of the Prior Art

In the field of medical catheters, especially in the areas of small vessel therapies, there has long been a need for extremely small diameter catheters with structural properties which cannot be attained with single substance structures. The most important property missing in small diameter catheters (4Fr and smaller) has always been "torqueability" and "pushability" or the ability to accurately transmit rotational and axially acting forces from the approximate proximal end to the approximate distal end for the purposes of steering during placement and for the accomplishment of therapies. In addition, there are some requirements for burst strength under pressure which exceed the properties of single substance constructions. Even multi-polymer structures in most cases do not generate composite properties at optimum levels for many uses.

In actual fact, balloon catheters have encountered thresholds which have limited the quest for ever-smaller arrangements. This is evidenced by the fact that, although high modulus reinforced catheters have been in demand, none have successfully reached the market in sizes below 4 French due to the inability to fabricate the same accurately, in volume, and at a price affordable to the medical trade.

U.S. Pat. No. 4,764,324 which was issued on Aug. 16, 1988 in the name of Burnham (one of two inventors named on the instant application) disclosed a technique for making small diameter catheter.

However, in attempting to apply the technique disclosed in U.S. Pat. No. 4,764,324 (hereinafter Burnham '324 and which is hereby incorporated by reference thereto) to the problem of manufacturing ultra small composite tubes, it was found that desired results could not be achieved. Burnham '324 discloses the steps of: preheating the polymer substrate to a controlled degree; applying reinforcement strands/electrical conductors with appropriate winding tension to cause the strands/conductors to sink below the original substrate surface to a controlled degree; and smoothing the remaining disrupted polymeric surface to reconstruct a smooth external surface.

When attempting to only partially soften the walls of tiny tubes in the range of 0.008" down to 0.0005" in wall thickness, it was found that the heat transfer rate of the polymer to be softened is so high that the lineal separation of the heating area and the strand application area caused total fusion of the polymer. The cause of this problem was found to reside in the fact that a given amount of time is required for the heated polymer substrate to move from the heating area to the strand application point and that this was too long and allowed the fusion to go beyond the partial stage at even the highest speeds. This excessive fusion allowed the reinforcing strands to totally penetrate the tube wall and come into physical contact with the internal supporting mandrel. In other words the strands wound up for all intents and purposes, all the way through the wall they were meant to reinforce midway.

SUMMARY OF THE INVENTION

It is an object of the present invention is to provide a technique which enables the production of very small diameter reinforced tubing which can be used as a catheter or the like, in an economical and reproducible manner.

During the development of the present invention, experiments to determine the nature of the failure mode of the Burnham '324 method, were conducted. One of the experiments was such that a tube of 0.044" outside diameter and 0.036" inside diameter was made by extruding Pebax 1147 SAOO, 72 D polymer over an acetal mandrel of 0.036" diameter, making a solid structure with a diameter of 0.044". (When the mandrel is removed after processing, the inside diameter will be the 0.036" of the formerly resident mandrel). In this case, 8 bobbins were loaded with 0.001" thick by 0.003" wide 304 stainless steel wire and mounted on the machine carriers.

A multiple-thousand foot roll of solid tube/mandrel structure was disposed under a machine designed to execute the Burnham '324 technique and threaded up, bottom to top, as follows: The end of the reeled tube/mandrel structure was carried up through the machine center through a brass guide tube and into and through an axial oven designed to apply radiant heat to the material passing through its center. This cylindrical oven performs the preheat stage of the Burnham '324 process, and is controllable on a continuing basis to within 1 degree F. at any setting up to 2100 degrees. At start-up, the oven as at room temperature to enable the insertion of the starting end.

At the exit point of the axial oven, the material was hand guided up to and through a wire guiding die with its hole co-axial with the oven and spaced a distance that is variable upward to allow manual access to the gap for threading purposes. Once through the upper guide die, the material was passed through an alignment guide and up onto a large diameter (2 feet) pulling wheel which pulls the tube/mandrel through the machine process at a controlled rate during execution of the process.

It will be understood that the rate of circumferential rotation of this pull wheel versus the heat intensity of the axial oven controls the degree of fusion of the polymeric strand passing through the machine.

Once the polymer strand was threaded, the machine was started at a rate of 2.28 feet per minute and the preheat oven set at 500 degrees. After 5 minutes of running strand through the machine with no wire being applied, the oven reached the correct temperature and stabilized. Since the upper wire guide die is also heatable by means of its holder, this was also started and set to a temperature of 350 degrees.

With all temperatures stabilized, the wire threading process was initiated. This was achieved by manually pulling individual ends of wire, one by one, off the carriers and wrapping them around the polymer structure by hand-spinning the round carrier table which holds all the wire bobbins. As soon as each individual end "grabbed" by passing up through the upper guide while the tension sank it into the softened polymer, the next one was done. This was repeated until eight ends were in place, 4 in each direction of rotation of the counter-rotating carrier plates. The machines rotation was then started with the carrier plates set at 342 rpm to yield a lay pitch of 0.020" center to center of the applied wires. As soon as the required rotation speed was reached, a first inspection was made of the wire pattern and the depth of embedment resulting from the heat/speed parameters set at start-up. This inspection showed that the 500 degree oven temperature was softening the entire polymer/mandrel structure and that the full dynamic pressure of all the wires wrapping down at the same time was causing the structure to collapse into a melted moving mass being dragged through the machine by the strength of the wires.

In an attempt to rectify this situation the preheat oven was switched off and the machine was allowed to continue with all other settings intact. As was anticipated, as the oven heat declined, the amount of embedment decreased. Unfortunately, the embedment while decreasing, suddenly changed from going all the way to the mandrel to the situation wherein it laid on the structure surface. This change was observed to occur over a temperature span of 5 degree or less.

As the oven temperature was controllable, the temperature was brought back up in 1 degree increments while monitoring the embedment dynamically and taking samples off the wheel at intervals. While this enabled a semblance of correct operation to be achieved, the embedment depth was observed to be so unstable as to render the technique useless for mass production. Viz., it was intended to embed two thicknesses of 0.001" wire (4 wires right hand in a layer, and 4 wires left hand in another layer) halfway through a polymer thickness of 0.004". Since the 2 wire layers consumed half of the wall, there was a total of 0.001" of polymer on each side of the wire structure. The middle 0.002" of polymer were radially coincident with the wire layers.

It was thus understood that the failure resulted from a non-uniform temperature and rate control. The Burnham '324 process when executed at the above tiny size, became thermally unstable due to tiny variant air currents in the tight confines of the machine and axial stretching of the heated structure. This caused the effective heating of the polymer strand to become uneven both circumferentially radially and longitudinally with the result that the wire "porpoised" continuously from totally through the wall to an equally useless position of laying on the surface. In addition, the lack of circumferential heat uniformity caused the wire to be embedded deeper in one wall than it was on the diametrically opposed wall. All of this in and out and all around variation combined to yield a decorative but useless "barber pole" spiral affect to the reinforcement pattern.

Once having identified the source of the problem a modified technique was struck upon.

In brief, the modified process was such that the reinforcing strands/material were wound, under a predetermined tension, onto ambient temperature tubing in which a mandrel has been inserted. Co-incident with this, the tubing and windings were simultaneously passed into a heated die which is so sized and configured as to compress the strands against the tubing and simultaneously apply both radiant and conducted heat. The third stage incorporated in the die design removed the compressive force and allowed radiant heat and the tension in the strands to carry the now flush-immersed strands to the required depth within the tubing wall.

More specifically, a first aspect of the invention resides in a method of forming small diameter reinforced tubing wherein reinforcing strands are wound under a predetermined tension onto ambient temperature mandrelized tubing. Simultaneously with this, the strands are compressed against the tubing and simultaneously heated via the application of both radiant and conductive heat by introduction into a die which is adapted to apply heat thereto. In this instance the die is sized and configured to produce an interference as the strands and the portion of the tube on which the strands are wound on enter a mouth of the die and thus produce a compression force which compresses the strands against and into the tubing. After this, the compressive force is removed allowing the radiant heat and the tension in the strands to move the strands to a predetermined position within the wall of the tubing.

A special feature of the above mentioned method resides in that it is applicable to tubing which has a diameter of 4 French or less or is applicable to any tube having walls of 0.010 inches or less.

Another aspect of the present invention resides in a method of forming a catheter wherein reinforcing strands/material under a predetermined tension is wound onto an ambient temperature monolithic mandrelized tubing and which tubing has a wall thickness on the order of 0.010 inches. This step is simultaneous with the strands being compressed against the tubing and simultaneously subjected to both radiant and conductive heat. This is achieved by introducing the tubing and windings into a die which is adapted to apply heat thereto and which is sized and configured so as to produce a compressive force as the strands and the portion of the tube on which the strands are wound, enter an initial portion of the die. Immediately after this, the compressive force is removed and radiant heat and the tension in the strands allowed to move the strands to a predetermined position within the wall of the tubing when the tubing and the strands which are wound, pass through a final portion of the die.

Yet another aspect of the invention comes in a method of forming a reinforced tubular product which comprises supplying an ambient temperature mandrelized monolithic tubing which has a wall thickness which is equal or less than a predetermined limit, to a die. This tubing has a plurality of strands of reinforcing material which is under a predetermined tension wound onto the tubing so that the strands are supported on the outer surface of the tubing and so that deformation of the outer surface is essentially absent. The die has a first portion which is sized so that as the tubing (on which the strands are wound) enters the same, the strands are compressed against the tubing and the outer surface of the tubing undergoes deformation with a timing which is essentially simultaneous with the winding operation. Heat is applied to the tubing so that the tubing softens and the strands sink and become immersed in the tubing wall. The next sequential portion of the die is sized so that the compressive force applied in the first portion is absent and is such that radiant heat is applied to the tubing therein. This allows the tension in the reinforcing strands to move the stands to a predetermined depth below the outer surface of the tubing before the polymer can cool.

A special feature of the above mentioned method resides in that the predetermined limit for mid-wall location is in the order of 0.010 inches, the reinforcing strands have a thickness of approximately 0.001 inches, and the first portion of the die is selected to have a diameter which is equal to the diameter of the ambient temperature monolithic tubing plus a variable portion of the thickness of the reinforcing strands in total layers.

A further feature of the invention resides in an apparatus for producing small diameter reinforced tubing which features: means for winding a plurality of reinforcing strands which are under a predetermined amount of tension onto premandrelized tubing; and a die for receiving the mandrelized tubing. In this instance, the die includes a first section which includes means for forcing the plurality of strands inwardly against the surface, and for simultaneously conductively and radiantly heating the portion of the tube in the first section. The die also includes a second section which is spaced from the surface of the tube and which includes means for radiantly heating the portion of the tube in the second section.

Still another feature of the invention resides in a catheter which comprises: a monolithic plastic tubing, the tubing having an outer diameter of essentially about 4 French or a wall thickness of 0.010 inches or less; and a plurality of reinforcing strands which are embedded between the inner and outer walls of the tubing.

Special features of the above mentioned catheter resides in the reinforcing strands being approximately 0.0001 inches to 0.002 inches thick and the wall thickness of the tubing in which the strands are embedded being approximately 0.001 inches to 0.010 inches thick.

The reinforcing strands can also be electrically conductive if so desired.

BRIEF DESCRIPTION OF THE DRAWINGS

The present invention will become more clearly appreciated as the disclosure of the present invention is made with reference to the accompanying drawings wherein:

FIG. 2 is a sectioned perspective view showing the manner in which the reinforcing strands are wound on a mandrelized tubular substrate just as it drawn into the die shown in FIG. 1.

DESCRIPTION OF THE PREFERRED EMBODIMENTS

Figure 1:
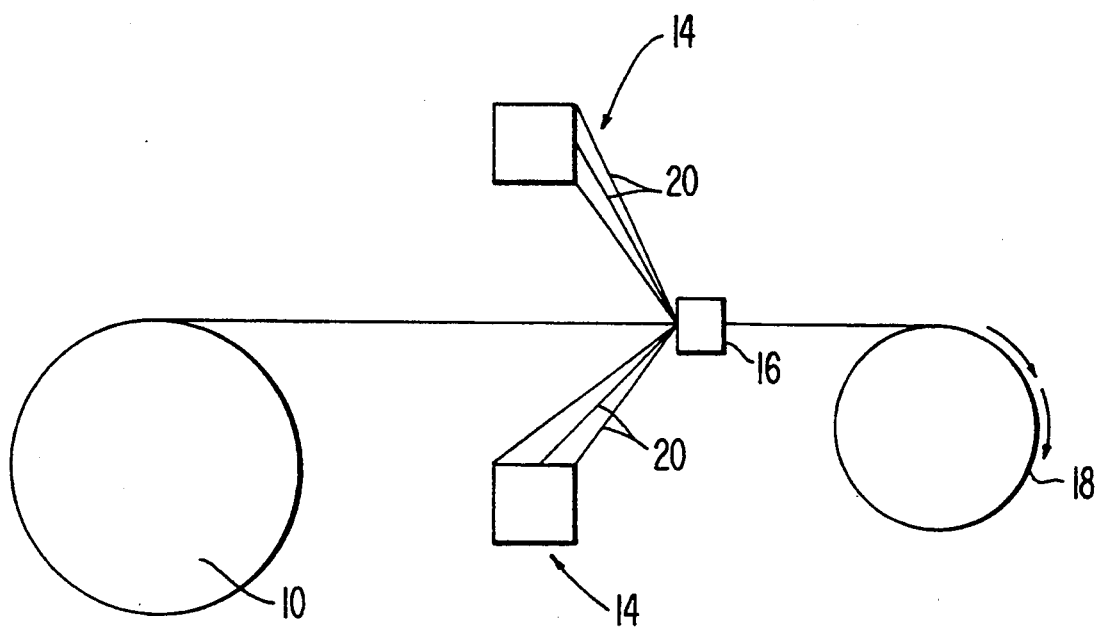
FIG. 1 schematically depicts the layout in which the die arrangement, which forms a vital part of the instant invention, is used when production according to the present invention is implemented.

FIG. 1 schematically depicts a possible layout by which the invention can be implemented. Briefly, this example is such as to include a supply of pre-mandrelized tubular product 10, means 14 for winding strands (20) of reinforcing material onto the mandrelized tubing under a predetermined amount of tension, a heated die 16, and a large diameter pulling wheel 18 (approx 2 feet in diameter) which is used to draw the product through the die 16 at a desired rate.

Figure 3A:
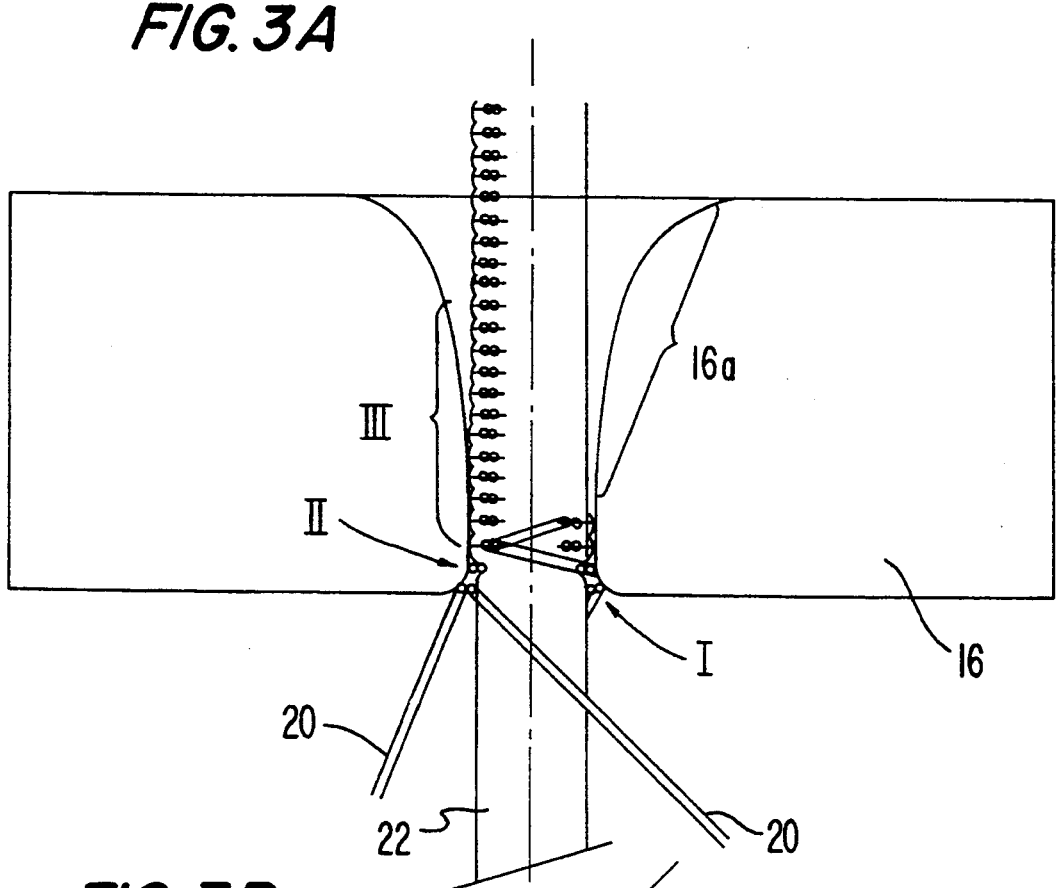
FIGS. 3A and 3B are schematic elevation and plan views showing details of the process depicted in FIG. 2, on an enlarged scale.
Figure 3B:
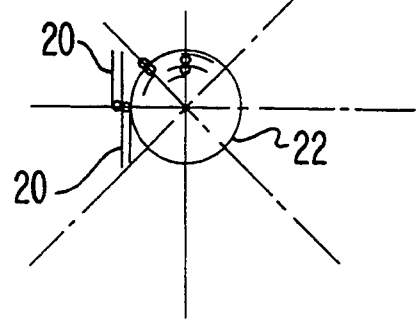

FIGS. 2, 3A and 3B depict the manner in which the reinforcing strands 20 are wound with a predetermined amount of tension onto the exterior of the plastic tube 22 immediately before entering the heated die 16. In this embodiment, the die responds to or is heated by RF energy and includes a RF guide 24 which is cast into the die proper. This arrangement allows the die to be heated to a predetermined level and accurately maintained thereat.

Alternatively, the die can be heated using a resistance heated die holder.

The process which characterizes the present invention includes three basic stages, I, II, and III (FIGS. 3A, 3B). The first stage (I) is such that all of strands of reinforcing material 20 are wound onto the exterior of a mandrelized tubing 22 just as it enters the mouth of the die. At this stage the effects of both radiant and conducted heat start to take place.

As best seen in FIGS. 3A and 3B, the inlet of the die is sized and configured such that during stage (II) which occurs as the just wound strands enter the bore, the strands are subjected to a compressive force and are forced inwardly against the tubing. At this stage, physical die compression in combination with radiant and conducted heating takes place. The external portion of the tube softens and allows the compression which is being applied to the strands to induce the latter to sink into the tubing to a "flush" depth.

The final section 16a of the die bore is arranged to progressively flare out in the illustrated manner. The third stage (III) of the process occurs as the tubing passes through this flared portion. More specifically, in this third stage, the physical compression and heating by conduction stop and the effects of radiant heat and strand tension induces all of the strands to travel further radially inward to reach the required depth within the tube wall.

The above process will become better appreciated as a description of a specific example is given along with comments relating to the various aspects of the process are given.

EXAMPLE

In accordance with the present invention, a run was set up in a manner wherein there was no heating by the preheat oven, and heat was applied only from the wire guiding upper die. In addition to this, the die size was chosen to be the exact diameter of the polymer strand plus a thickness of wire. In this particular case, 0.044"+0.001".

This resulted in an intentional diametral interference at the die opening of 0.003", since the base structure plus 2 wire layers per side equals 0.048". This was done to cause radial compression so that heat would be transmitted to the substrate by conduction through the wire as well as radiantly within the die's cylindrical length (Stage II) with that length serving as a super small axial oven located at the wire impingement point rather than ahead of that point by a given distance. It was reasoned that if the wire and substrate heating were accomplished simultaneously, advantage could be taken of the fact that any very thin wall heats up and softens extremely rapidly.

As both the throughput rate of the substrate through the die and the wire deposition rate were variable in order to maintain the correct geometry of lay, it was possible to appropriately select the rates in combination with the amount of heat produced by the upper die, in a manner which rendered it possible to achieve a set of operating parameters which would control the wire pattern as to both geometry and depth of penetration.

This process was observed to not only produce the desired results wherein the location of the wires is exactly "midwall" at 480° F. die heat, but also provided another unexpected bonus. Viz., no matter how much effort is made in extrusion, the polymer substrate can never have the mandrel perfectly centered therein. At the sizes contemplated in accordance with the present invention, even 0.001" eccentricity is a major error while in an ordinary sized tube it is acceptable variation within tolerances.

However, with the present invention as physical compression, conductive heating, and radiant heating all happen simultaneously in a tiny space, the depth of wire penetration is governed by these parameters working uniformly in from the outer circumference on an essentially cold substrate which has had no opportunity to change softness/viscosity values until the instant of wire insertion. The result is absolute uniformity of depth of wire penetration regardless of random variations in wall thickness around the circumference of the structure. In addition, since all the fusion heat comes from one tightly controlled source, is applied over a structure length of 1 to 8 structure diameters, and is done in less than 0.1 seconds per wire width of axial length, the controllability of wire location and penetration borders on being essentially absolute.

It should be appreciated that while the above disclosed process finds highly advantageous application with small diameter thin walled tubing, in situations wherein it is desired to achieve a mid-wall disposition of the reinforcing strands, the process is not limited with respect to diameter and can be applied to larger diameter tubes which have a thin wall. Alternatively, the process can be applied to thicker walled tubing in situations wherein it is desired to set the reinforcing strands in a shallow disposition just below the surface of a relatively thick wall.

At required reinforcing depths greater than those contemplated in accordance with the present invention (deeper than 0.004"-0.005" on any diameter structure), pre-heating is necessary to soften the substrate deeply enough for correct strand placement while using heating rates within the tolerance range of the structure's polymer. Viz., if the desired structure requires that the reinforcement/conductors be placed deeper than 0.004"/0.005" on any diameter structure, the heat required in the top die heat only mode gets to be so high as to degrade the polymer structure when run at any economical production rate.

It will be appreciated that the present invention is by no way limited to the specific embodiment disclosed and various changes and modifications can be made without departing form the scope of the present invention. For example, the die heating technique need not be limited to RF type heating and various other techniques could be envisaged either alone or in combination.

I claim:

1. A method of forming small diameter reinforced tubing comprising the steps of:
   winding reinforcing strands under a predetermined tension onto ambient temperature tubing in which a mandrel has been inserted;
   introducing said tubing with said reinforcing strands wound thereon into a die, said die being adapted to apply both radiant and conductive heat thereto, said die being sized and configured to produce an interference as the strands and the portion of the tube on which the strands are wound enter a mouth of said die, thereby producing a compression force which compresses the strands against said tubing simultaneously as said strands and said tubing are simultaneously heated by both radiant and conductive heat from said die; and
   removing the compressive force and allowing said radiant heat and the tension in the strands to move the strands to a predetermined position within a wall of the tubing.

2. The method as set forth in claim 1, further comprising the steps of:
   controlling a rate at which the tubing is passed through said die; and
   controlling a rotational speed of means which winds said strands onto said tubing, in accordance with the rate at which the tubing is passed through said die.

3. The method as set forth in claim 1, further comprising the steps of:
   using an RF responsive die; and
   heating the die using RF energy.

4. The method as set forth in claim 1, wherein the wall of said tubing has a thickness of 0.010 inches or less.

5. A method of forming a catheter comprising the steps of:
   winding reinforcing strands under a predetermined tension onto ambient temperature monolithic tubing in which a mandrel has been inserted, said tubing having a wall having a thickness on the order of 0.010 inches;
   introducing the tubing and the strands which are wound thereon into a die which is adapted to apply heat thereto, said die being so sized and configured as to produce a compressive force which compresses the strands against said tubing as the strands and the portion of the tube on which the strands are wound, enter an initial portion of said die and are simultaneously heated by both radiant and conductive heat from said die; and
   removing the compressive force and allowing radiant heat from said die and the tension in the strands to move the strands to a predetermined position within the wall of the tubing when the tubing and the strands which are wound, pass through a final portion of said die.

6. A method of forming a reinforced tubular product comprising the steps of:
   supplying an ambient temperature mandrelized monolithic tubing to a die, said tubing having a wall, said wall having a wall thickness which is equal to or less than a predetermined wall thickness;
   winding a plurality of strands of reinforcing material under a predetermined tension onto said tubing so that said strands are supported on the outer surface of said tubing and so that deformation of said outer surface is essentially absent;
   sizing a first portion of said die so that said strands are compressed against the tubing and the outer surface of said tubing undergoes deformation, as tubing on which said strands are wound, enters said first portion of said die;
   applying heat to the tubing and the strands within said first portion of said die via conduction and radiation, thereby softening said tubing and causing said strands to sink and become immersed in the tubing wall;
   sizing a second portion of said die so that the compressive force applied in said first portion is absent;
   applying radiant heat to the tubing within said second portion of said die; and allowing the tension in said reinforcing strands to move the strands to a predetermined depth below the outer surface of said tubing.

7. The method as set forth in claim 6, wherein said predetermined wall thickness is in the order of 0.010 inches, wherein said reinforcing strands have a thickness of approximately 0.001", wherein the first portion of said die is selected to have a diameter which is equal to the diameter of said ambient temperature monolithic tubing plus the thickness of one of said plurality of reinforcing strands.

* * * * *